US00PP37373P3

(12) United States Plant Patent
Holtmaat

(10) Patent No.: US PP37,373 P3
(45) Date of Patent: Apr. 14, 2026

(54) ***HEUCHERA* PLANT NAMED 'HEUSPI856'**

(50) Latin Name: ***Heuchera* hybrid**
Varietal Denomination: 'HEUSPI856'

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 19/318,063

(22) Filed: Sep. 3, 2025

(65) Prior Publication Data

US 2026/0101831 P1 Apr. 9, 2026

(30) Foreign Application Priority Data

Oct. 8, 2024 (QZ) ..... PBR 20242149

(51) Int. Cl.
*A01H 6/80* (2018.01)
*A01H 5/02* (2018.01)

(52) U.S. Cl.
USPC ..... Plt./440

(58) Field of Classification Search
USPC ..... Plt./440
CPC ..... A01H 6/80; A01H 5/02
See application file for complete search history.

*Primary Examiner* — Keith O. Robinson
(74) *Attorney, Agent, or Firm* — Penny J. Aguirre

(57) ABSTRACT

A new cultivar of *Heuchera* plant named 'HEUSPI856' that is characterized by its unique foliage colors; a blend of brown and gray with a blend of dark gray-green and black in area adjacent to the veins, its floriferous habit with dark pink-red flowers, its healthy and sturdy plant habit, and its growth habit that fills the container from the center to the edges.

3 Drawing Sheets

Botanical classification: *Heuchera* hybrid.
Cultivar designation: 'HEUSPI856'.

CROSS REFERENCE TO A RELATED APPLICATIONS

This application claims priority to European Community Plant Variety Office (CPVO) Plant Breeder's Rights Application No. 2024/2149 filed on Oct. 8, 2024, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Heuchera* of hybrid origin, botanically known as *Heuchera* 'HEUSPI856' and is hereinafter referred to by its cultivar name 'HEUSPI856'.

The new cultivar originated as a seedling that arose from seed planted from open pollination of an unnamed and unpatented plants of *Heuchera* from the Inventor's breeding program in Zuidwolde, Netherlands. The seeds were pooled from the crosses and therefore the parents of the new cultivar are unknown. 'HEUSPI856' was selected as a single unique plant in July of 2021 from the resulting seedlings.

Asexual propagation of the new cultivar was first accomplished under the direction of the Inventor by tissue culture initiated from meristem tissue in June of 2022 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HEUSPI856' as a new and unique cultivar of *Heuchera*.

1. 'HEUSPI856' exhibits unique foliage colors; a blend of brown and gray with a blend of dark gray-green and black in area adjacent to the veins.
2. 'HEUSPI856' exhibits a floriferous habit with dark pink-red flowers.
3. 'HEUSPI856' exhibits a healthy and sturdy plant habit.
4. 'HEUSPI856' exhibits a growth habit that fills the container from the center to the edges.

'HEUSPI856' can be most closely compared to the *Heuchera* cultivars 'Can Can' (not patented) and 'World Caffe Corretto' (not patented). 'Can Can' is similar to 'HEUSPI856' in leaf coloration. 'Can Can' differs from 'HEUSPI856' in having leaves with deeper lobes and are more undulate and flowers that are lighter in color. 'World Caffe Corretto' differs from 'HEUSPI856' in having foliage that is slightly coarser in texture, slightly more undulate with deeper lobing, and light grey to gray-green in color, and flowers that are creamy white in color.

BRIEF DESCRIPTION OF THE DRAWINGS

The accompanying color photographs illustrate the overall appearance and distinct characteristics of the new *Heuchera*. The photographs were taken of a 8-month-old plant of 'HEUSPI856' as grown outdoors in 19-cm containers in Heerhugowaard, Netherlands.

The photograph in FIG. 1 provides a side view of 'HEUSPI856' in bloom.

Figure 1:
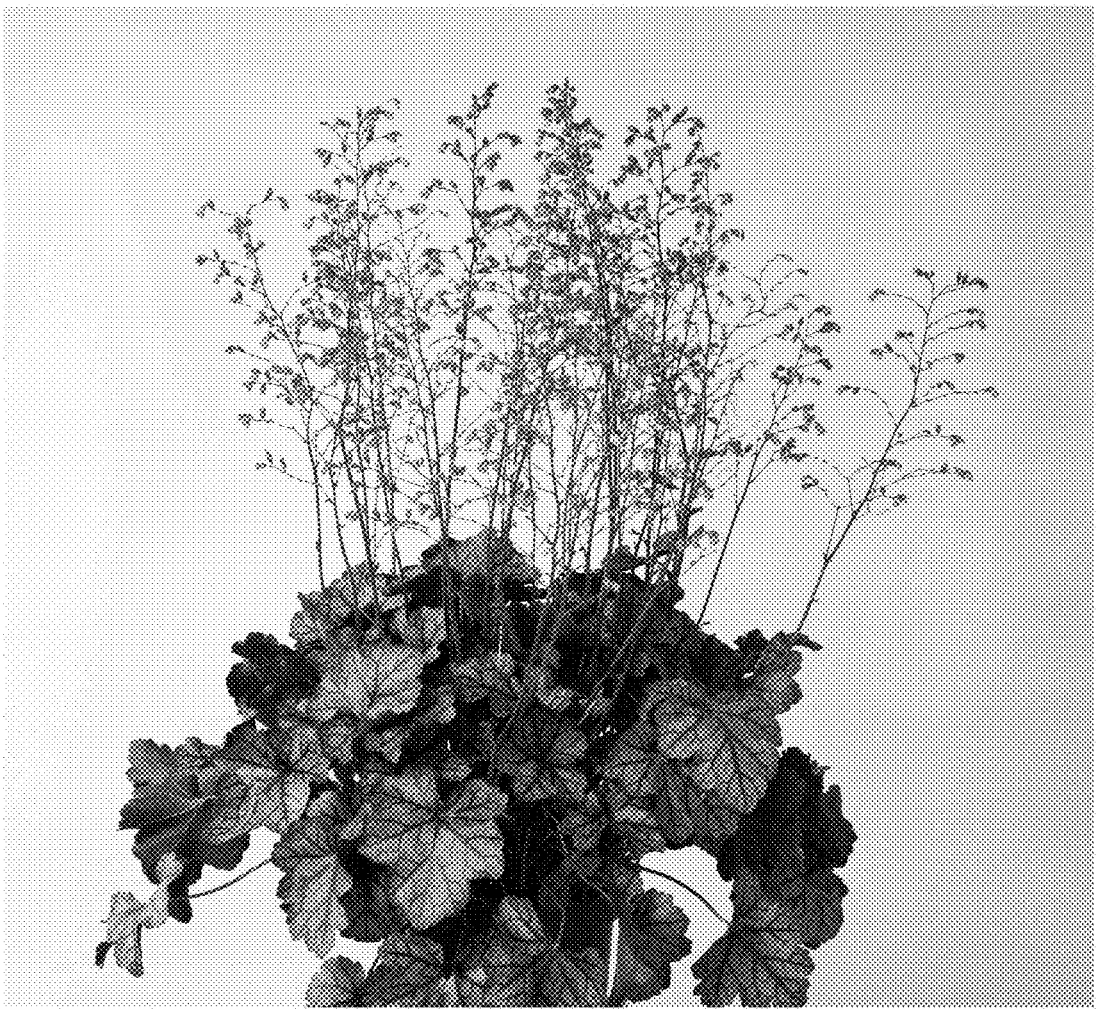
Figure 2:
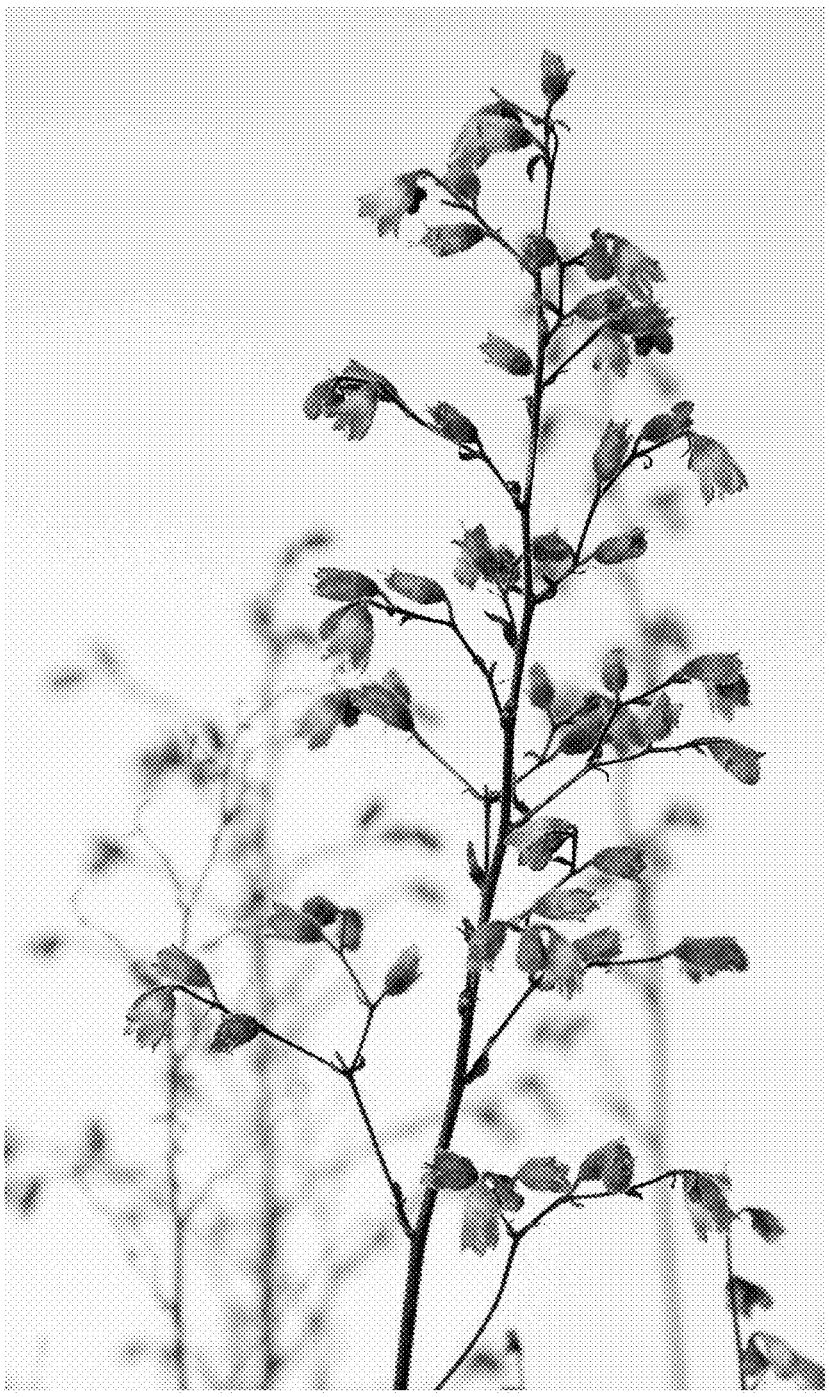

The photograph in FIG. 2 provides a close-up view of an inflorescence of 'HEUSPI856'.

Figure 3:
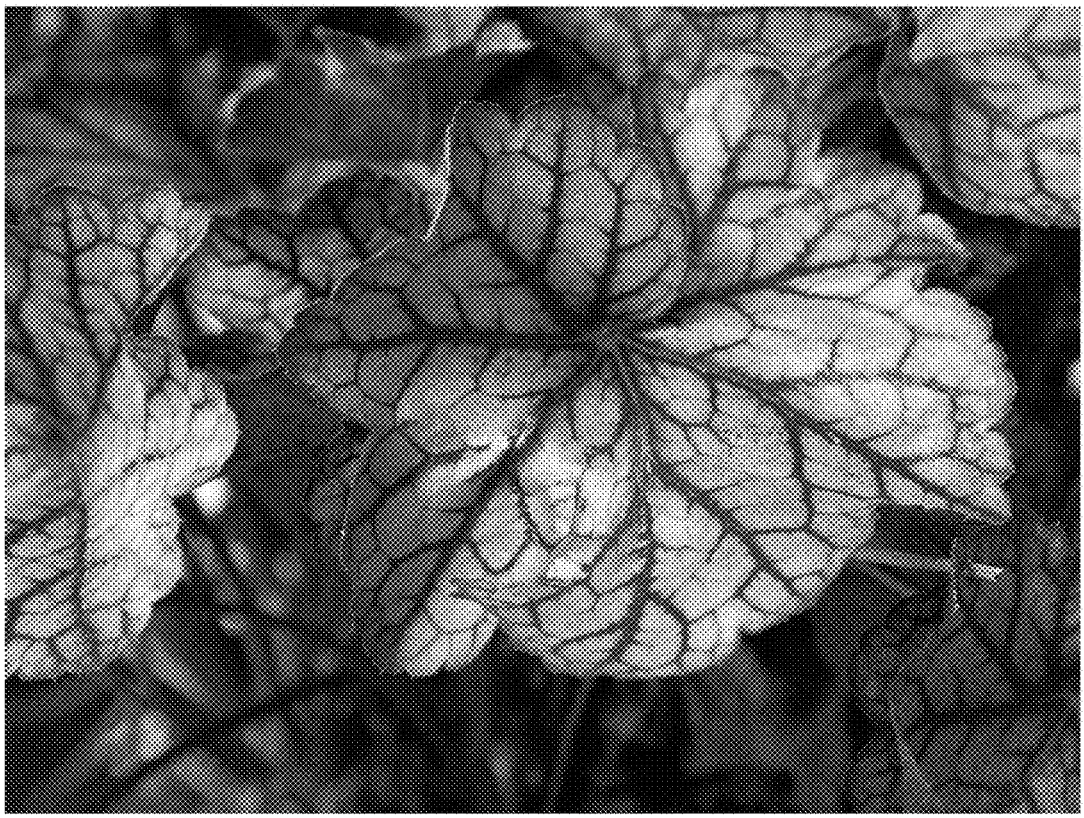

The photograph in FIG. 3 provides a close-up view of the foliage of 'HEUSPI856'.

The colors in the photograph are as close as possible with the digital photography techniques available, the color values cited in the detailed botanical description accurately describe the colors of the new *Heuchera*.

BOTANICAL DESCRIPTION OF THE PLANT

The following is a detailed description of 8-month-old plants of 'HEUSPI856' as grown in 19-cm containers outdoors in Heerhugowaard, Netherlands. The phenotype of the new cultivar may vary with variations in environmental, climatic, and cultural conditions, as it has not been tested under all possible environmental conditions. The color determination is in accordance with The 2015 Colour Chart (2019 reprint) of The Royal Horticultural Society, London, England, except where general color terms of ordinary dictionary significance are used.

General description:

*Blooming period.*—10 weeks from midsummer to late summer in The Netherlands.

*Plant type.*—Herbaceous perennial.

*Plant habit.*—Flattened globular with inflorescences held above the foliage.

*Height and spread.*—An average of 32.9 cm in height (soil level to top of foliar plane), average of 65.9 cm in height (soil level to top of floral plane) and 62.5 cm in spread as an 8-month-old plant grown in a container.

*Hardiness.*—At least in U.S.D.A. Zones 3 to 9.

*Diseases and pests.*—No susceptibility or resistance to pests or diseases has been observed.

*Root description.*—Fibrous roots on woody rootstalks.

*Propagation.*—Tissue culture.

*Root development.*—An average of 3 weeks for root initiation, 6 weeks to produce a rooted cutting.

*No. of basal rosettes per plant.*—24.

*Growth rate.*—Vigorous.

Stem description; None present, leaves emerge as basal rosettes from roots.

Foliage description:

*Leaf shape.*—Broad ovate to near orbicular in outline, slightly to moderately concave.

*Leaf division.*—Simple.

*Leaf base.*—Hastate, lobes touching to very slightly overlapping.

*Leaf apex.*—Acute.

*Leaf venation.*—Laciniate, upper surface color 197A, lower surface 186C in color.

*Leaf margins.*—Crenate with abruptly acute tips on each tooth, moderately to strongly coarsely undulate.

*Leaf attachment.*—Petiolate.

*Leaf arrangement.*—Alternate in basal rosettes.

*Leaf lobes.*—Lobed, an average of 7 lobes, occasionally 9, shallow to medium in depth, divergent, lobe margins free.

*Leaf surface.*—Both surfaces non-rugose, upper surface matte to very slightly glossy, lower surface slightly glossy, upper surface densely covered with very short strigose hairs 0.3 mm in length, lower surface sparsely to moderately covered with very short strigose hairs 0.5 mm in length, hairs on both sides NN155D in color.

*Leaf color.*—Young upper surface; a blend of 197A and 201A, veined 182A, young lower surface; N186D, mature upper surface; a blend of N200B and 201A, area adjacent to main veins and secondary veins is 202A, tinged N189A, mature lower surface 187B.

*Leaf size.*—An average of 12.3 cm in length and 11.7 cm in width.

*Leaf quantity.*—An average of 8 per basal rosette.

*Petioles.*—An average of 18.9 cm in length and 3 mm in diameter, medium strength, both surfaces moderately glossy, upper surface color a blend of 183A and 187A, lower surface color 183A, very sparsely covered with short soft hairs; 0.5 mm in length, and densely covered with a very short, glandular pubescence with hairs too small to measure color.

*Stipules.*—Leafy stipules at the base of each leaf, average of 2.1 cm in length and 0.7 cm in width, apex acute, matte surface, 187B in color.

Flower description:

*Inflorescence type.*—Numerous small bell-shaped flowers arranged on panicles on peduncles emerging from a basal rosette.

*Inflorescence size.*—An average of 26.6 cm in height and 12.3 cm in diameter.

*Inflorescence number.*—An average of 3.

*Flower fragrance.*—None.

*Flower quantity.*—Average of 140 flowers per inflorescence, 4,000 flowers per plant, 750 buds and flowers per plant.

*Flower lastingness.*—Average of one week.

*Flower buds.*—Obovate in shape, an average of 6 mm in length and 3 mm in diameter, 58B in color, surface is matte and moderately covered with very short glandular hairs; an average of 0.3 mm in length and too small to measure color.

*Flower aspect.*—Outward to slightly nodding.

*Flower type.*—Single, campanulate.

*Flower size.*—Average of 7 mm in diameter and 1 cm in length.

*Petals.*—Average of 5, oblanceolate in shape, margin is entire, acute apex, base long acuminate, upper and lower surface is glabrous, smooth and matte, an average of 4 mm in length and 1 mm in width, color when opening upper surface; 68D, color when opening lower surface; 68B, margins and top 68C and 68D, fully open upper surface; 68D, fully open lower surface; 68C, margins and top 68D.

*Calyx.*—Campanulate, sepals fused to hypanthium, 1 mm in length, 7 mm in diameter.

*Sepals.*—An average of 5, lower 60% fused into campanulate hypanthium, free part ovate in shape, an average of 1 cm in length and 0.4 mm in width, margin entire, base fused into hypanthium, apex is broadly to bluntly acute, color; when opening and fully open upper surface; 55A, base 55B, fused with 62C, when opening and fully open lower surface; 55A, base 55B, fused portion 54A.

*Peduncle.*—An average of 60.4 cm in length and 3 mm in diameter, N186C in color, primary flower aspect 65°, secondary peduncle aspect 35° to main peduncle moderate in strength, surface moderately glossy and moderately covered with very short soft glandular hairs; average of 0.3 mm in length, N155D in color.

*Pedicels*.—An average of 3.5 mm in length and 0.5 mm in diameter, 183A in color, primary flower aspect straight on top of secondary pedicel, secondary and tertiary flower aspect an average of 40° to pedicel, moderate in strength, surface matte and moderately covered with very short soft glandular hairs; average of 0.3 mm in length and to small too measure color.

Reproductive organs:

*Gynoecium*.—Pistils; 2, 5 mm in length, stigma; club-shaped, too small to measure color, 0.2 mm in diameter, style; an average of 4.75 mm in length, color; NN155C, ovary; 155A in color.

*Androecium*.—Stamens; 5, anthers; ovate in shape, average of 0.3 mm in length and width, 160C in color, filament; 3 mm in length and NN155D in color, pollen; low in quantity and 155B in color.

*Seed/fruit*.—No fruit or seeds have been observed to date.

It is claimed:

1. A new and distinct cultivar of *Heuchera* plant named 'HEUSPI856' as herein illustrated and described.

* * * * *